(12) United States Patent
Eloranta et al.

(10) Patent No.: US 6,718,191 B2
(45) Date of Patent: Apr. 6, 2004

(54) SKIN POTENTIAL MEASURING SENSOR

(75) Inventors: Mikko Eloranta, Kuopio (FI); Olli Pohjolainen, Kuopio (FI)

(73) Assignee: Medikro Oy, Kuopio (FI)

( * ) Notice: Subject to any disclaimer, the term of this patent is extended or adjusted under 35 U.S.C. 154(b) by 0 days.

(21) Appl. No.: 09/877,189

(22) Filed: Jun. 11, 2001

(65) Prior Publication Data

US 2001/0029327 A1 Oct. 11, 2001

Related U.S. Application Data

(63) Continuation of application No. 09/704,788, filed on Nov. 3, 2000, now abandoned, which is a continuation of application No. PCT/FI99/00369, filed on May 4, 1999.

(30) Foreign Application Priority Data

May 4, 1998 (FI) .................................................. 980989

(51) Int. Cl.[7] ................................................. A61B 5/04
(52) U.S. Cl. ........................ 600/372; 600/546; 600/547; 128/902; 128/903
(58) Field of Search ................................ 600/372, 382, 600/393, 395, 546, 547; 128/903, 902

(56) References Cited

U.S. PATENT DOCUMENTS

| | | | | |
|---|---|---|---|---|
| 3,500,823 A | * | 3/1970 | Richardson | 600/372 |
| 3,565,060 A | * | 2/1971 | Sipple | 128/902 |
| 3,605,728 A | * | 9/1971 | Ogle | 128/908 |
| 3,620,208 A | * | 11/1971 | Higley et al. | 600/395 |
| 3,628,527 A | * | 12/1971 | West | 330/1 R |
| 3,744,482 A | * | 7/1973 | Kaufman et al. | 600/372 |
| 4,669,479 A | * | 6/1987 | Dunseath, Jr. | 128/902 |
| 4,791,936 A | | 12/1988 | Snell et al. | |
| 4,996,989 A | * | 3/1991 | Stundel et al. | 600/383 |
| 5,513,636 A | | 5/1996 | Palti | |
| 5,862,803 A | * | 1/1999 | Besson et al. | 128/903 |
| 6,285,899 B1 | * | 9/2001 | Ghaem et al. | 128/903 |

FOREIGN PATENT DOCUMENTS

| | | |
|---|---|---|
| DE | 196 07 222 | 8/1997 |
| WO | WO 89/02247 | 3/1989 |
| WO | WO 95/07048 | 3/1995 |

* cited by examiner

*Primary Examiner*—Lee Cohen
(74) *Attorney, Agent, or Firm*—Pillsbury Winthrop LLP

(57) ABSTRACT

A skin potential measuring sensor includes a measuring electrode to be placed on the skin and a signal transfer element attached thereto. The elements which measure, handle and digitize the signal in order to convert it into a digital signal are placed close to the measuring electrode.

15 Claims, 3 Drawing Sheets

SKIN POTENTIAL MEASURING SENSOR

This is a Continuation of National application Ser. No. 09/704,788 filed Nov. 3, 2000, now abandoned, which was a Continuation of. International Application No. PCT/FI99/00369 filed May 4, 1999 which designated the U.S.

BACKGROUND OF THE INVENTION

1. Field of the Invention

The present invention relates to a skin potential measuring sensor which comprises a measuring electrode with a signal transfer attachment, to be placed on the skin.

2. Description of Related Art

When measuring skin potential and transferring the measured values analogically, a special wire is required to minimize capacitative and inductive interference induced from the surroundings. If unshielded electrode cabling is used, error signals from interfering electromagnetic sources will be induced to the wires. The error signals can be stronger than the actual skin potential signal. Each wire should therefore be individually screened against interference, which in turn causes the wiring system to become complicated, heavy and expensive. Moving and bending a shielded wire will generate electrical noise when the wire shield moves in relation to the wire conductor and the insulation material (microphonism of the wire). When a high impedance signal is transferred inside a long cable, the resistance, capacitance and inductance of the cable will cause change to the amplitude of the signal and the response frequency. Different skin potential signals can also interfere with one another in the wiring system (crosstalk).

SUMMARY OF THE INVENTION

The object of the invention is to provide a skin potential measuring sensor, with which the present disadvantages related to skin potential measuring sensors, and especially problems due to error signals and screening, will be eliminated. In particular, the object of the invention is to provide a skin potential measuring sensor, which sensor can directly be connected to a digital data processing system via a digital data transmission system.

The object of the invention is accomplished by means of a skin potential measuring sensor, the characteristics of which are set forth in the claims.

In a skin potential measuring sensor according to the invention, the elements required for measuring, processing and digitizing the signal from the measuring electrode are located close to the electrode. By placing the signal measuring, processing and digitizing elements into close vicinity of the measuring electrode, according to the invention, the measured analogic skin potential signal can be converted into a digital signal without any transfer wires. When the measurement is taken directly from the electrode, a numeric signal can reliably be transferred inside the conventional wires and the errors caused by the wires can be eliminated. Thus, no special wires are needed.

The signal transfer element has been designed to transfer the measured signal in a digital form through the data transmission system to the main processor. Thus, the skin potential sensor can directly be connected to a digital data processing system.

In one embodiment of the invention, the system is arranged so that the sampling of the measuring signals from different sensors is synchronous. The simultaneity makes numeric calculation (i.e. adding and subtraction) of different signals possible. Further numeric processing makes it possible to form new signals through calculations (without additional electronics) from measured signals from different sensors. If the sampling is not synchronous, the calculated signal may be significantly distorted.

BRIEF DESCRIPTION OF THE DRAWINGS

Next, the invention will be described in more detail with reference to the accompanying drawings, in which.

DETAILED DESCRIPTION

Figure 1:
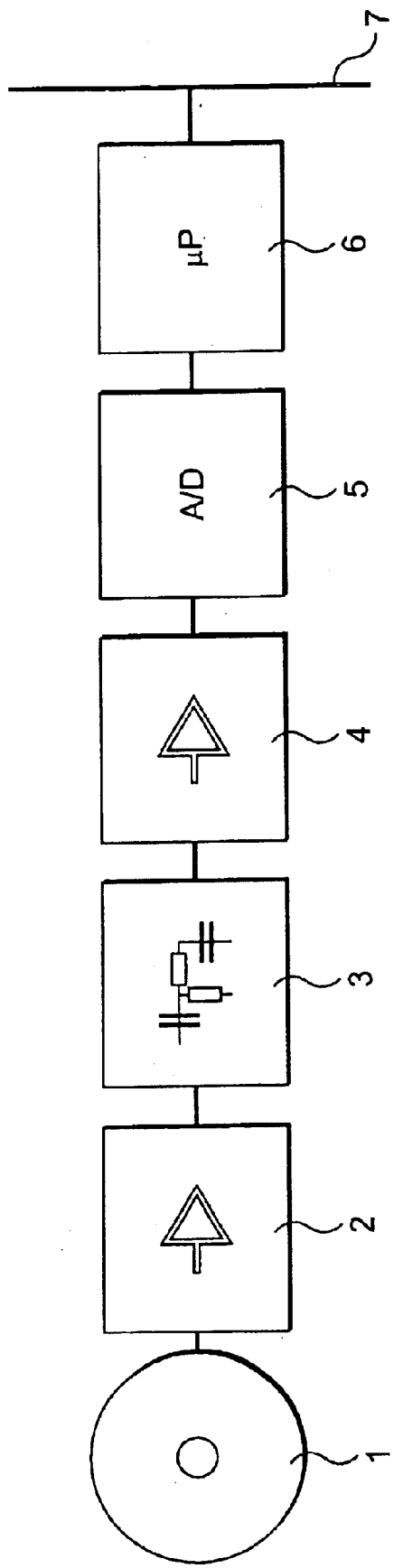
FIG. 1 illustrates a block diagram of a digital skin potential measuring sensor according to the invention.

In the block diagram according to FIG. 1, part 1 illustrates the measuring electrode on the surface of the skin. The signal is being led from the measuring electrode to part 2, which contains a buffer amplifier, which prevents loading of the high impedance electrode signal. Part 3 contains high pass and low pass filtering, which filter the noise signals that are outside of the measuring range and the offset-voltage from the electrode. Part 4 amplifies the signal so that it is strong enough. Part 5 converts the analogue signal to a digital one and part 6 contains the digital processing of the signal as well as the connection to the data transfer network. Part 7 contains the cabling for the data transfer network.

Figure 2:
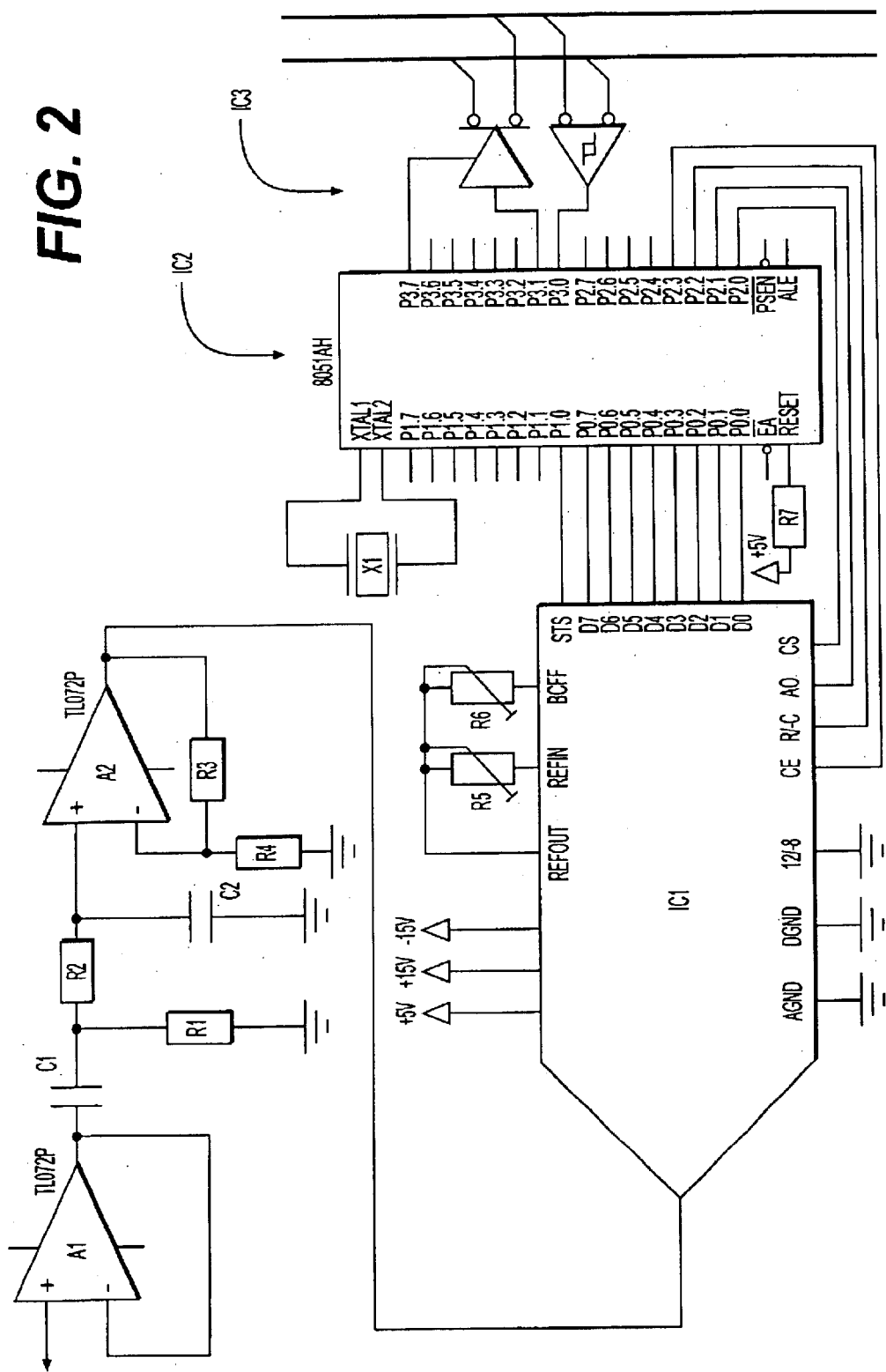
FIG. 2 illustrates one embodiment of an electronic digital skin potential measuring sensor.

In a configuration according to FIG. 2, the operation amplifier A1 forms a buffer amplifier, which prevents the loading of the high impedance signal. The gain of the buffer amplifier is +1. The capacitor C1 and the resistor R1 form a high pass filter and the resistor R2 and the capacitor C2 form a low pass filter. The filters filter noise signals that are outside of the measuring range. The operation amplifier A2 forms together with the resistors R3 and R4 an amplifying non-inverting amplifier, with which the signal is amplified to a sufficient level. The amplification of the amplification stage can be calculated from the formula $G=(1+R3/R4)$. IC1 is an A/D converter, which converts the analogue signal to a digital signal. The resistor R5 is used for the fine adjustment of the amplification and R6 for the fine adjustment of the zero level. IC2 is the microprocessor which controls the conversion and possibly also analyzes the signal. IC3 forms the buffer stage in the data transfer channel.

Figure 3:
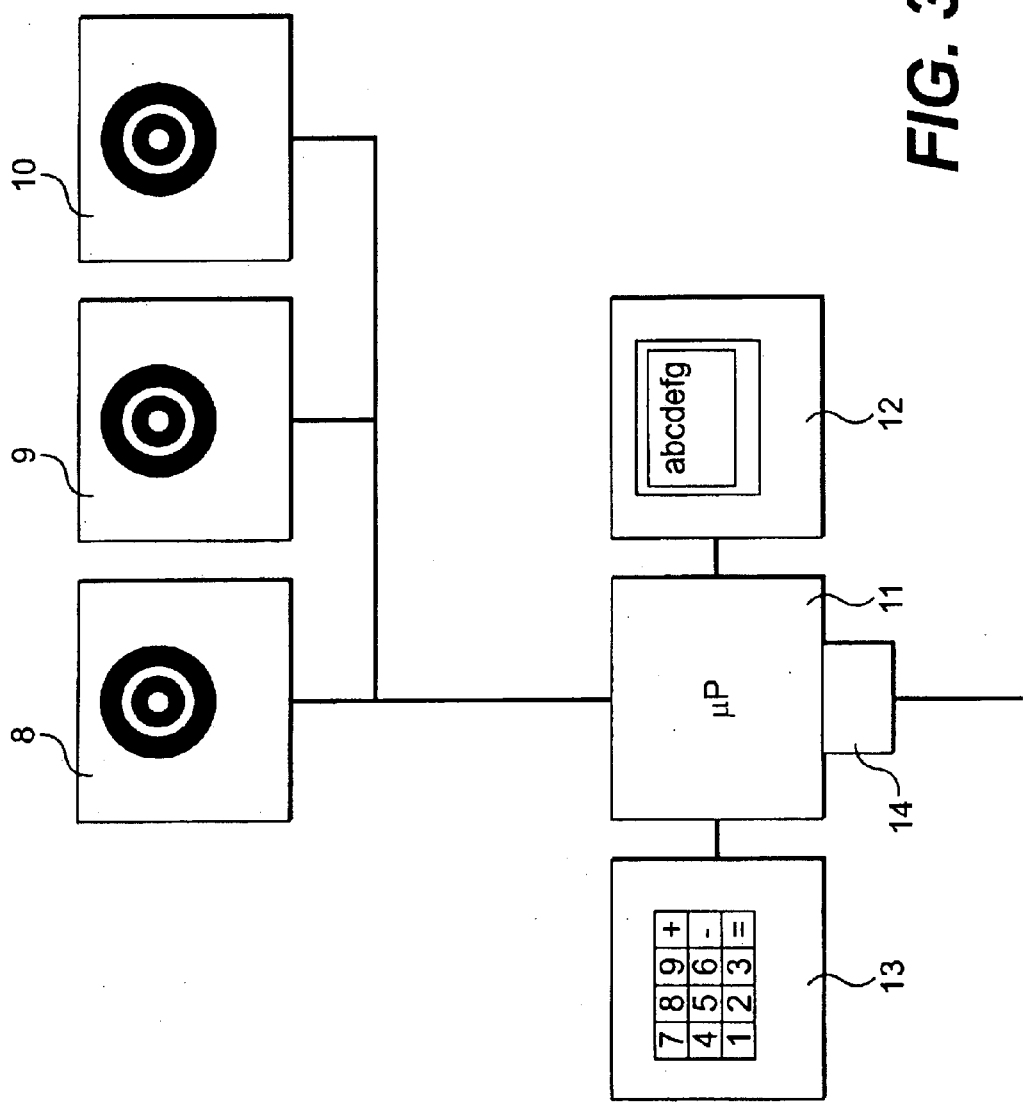
FIG. 3 illustrates a block diagram of a system comprised of several sensors.

In a block diagram according to FIG. 3, several skin potential measuring sensors have been connected to each other. Parts 8 and 9 are digital skin potential measuring sensors, part 10 is the potential equalizing connection, and part 11 is the main processing unit which controls the network and which may also contain a display 12 and a keyboard 13. The main processing unit controls the digital sensors through the data transfer network and collects the data from the digital sensors. Collected and possibly analyzed data can also be transferred to other systems through the data transfer part 14.

The invention is not limited to the embodiments set forth in the application. The invention is versatile and it can vary within the frame of the idea of the invention put forth in the claims Additional Information This patent application is made to protect a technology, which enables reduced costs to build a scalable multi-channel skin potential measurement system with simultaneous signal sampling. To build the measurement system it is possible to connect multiple (=easy to scale) identical or different skin potential sensors together with the data network cable. There is no need to use analogue electrode cable, because each sensor is placed on the electrode at the measurement point. The data transfer from the sensor network to the application computer can be realised with different known technologies (e.g. telemetric), and our patent application uses one of these as an application example. This solution presents a distributed and network based measuring architecture, which is a key idea of our patent application.

The signal of the electrode is amplified, filtered and digitized in a skin potential measuring sensor in close vicinity of the electrode (normally a single use electrode) without the need of the analogue signal transferring cable.

From each skin potential measuring sensor the data is transferred in the digital form via a digital network cable. All the sensors are connected to this network cable.

The network cable that connects the skin potential measuring sensors includes a signal that is used to start the measurement in all the skin potential measuring sensors at the same time. In this distributed architecture all the sensors connected to the system amplify, filter and digitize the electrode signals at the same time and independently.

What is claimed is:

1. A skin potential measuring sensor, comprising:
   a measuring electrode configured to be placed on the skin at a measurement point to provide an analog signal;
   a data processing system placed on and connected directly to the measuring electrode at the measurement point, wherein the data processing system is configured to measure, process, and digitize the analog signal provided by the measuring electrode to provide a measured digital signal, the data processing system consisting essentially of a buffer amplifier connected in series to high pass and low pass filters connected in series to a non-inverting amplifier connected in series to an analog to digital converter connected in series to a digital processor; and
   a signal transfer element connected to the data processing system and configured to transfer the measured digital signal.

2. The skin potential measuring sensor of claim 1, further comprising a data transfer network, wherein the signal transfer element is configured to interface with the data transfer network to transfer the measured digital signal in a digital form to the data transfer network.

3. The skin potential measuring sensor of claim 2, wherein:
   the data transfer network is configured to transfer to the signal transfer element a synchronous signal; and
   the data processing system is configured to begin measuring, processing, and digitizing upon receiving the synchronous signal.

4. The skin potential measuring sensor of claim 1, wherein:
   the signal transfer element is configured to transfer to the data processing system a synchronous signal; and
   the data processing system is configured to begin measuring, processing, and digitizing upon receiving the synchronous signal.

5. The skin potential measuring sensor of claim 1, wherein the data processing system is connected directly to the measuring electrode such that the analog signal can be converted to the measured digital signal without using analog electrode cable.

6. A skin potential measuring sensor, comprising:
   a measuring electrode configured to be placed on the skin at a measurement point to provide an analog signal;
   a data processing system placed on and continuously connected directly to the measuring electrode at the measurement point, wherein the data processing system is configured to measure, process, and digitize the analog signal provided by the measuring electrode to provide a measured digital signal and the data processing system is connected directly to the measuring electrode such that the analog signal can be converted to the measured digital signal without using analog electrode cable; and
   a signal transfer element connected to the data processing system and configured to transfer the measured digital signal.

7. The skin potential measuring sensor of claim 6, further comprising a data transfer network, wherein the signal transfer element is configured to interface with the data transfer network to transfer the measured digital signal in a digital form to the data transfer network.

8. The skin potential measuring sensor of claim 7, wherein:
   the data transfer network is configured to transfer to the signal transfer element a synchronous signal; and
   the data processing system is configured to begin measuring, processing, and digitizing upon receiving the synchronous signal.

9. The skin potential measuring sensor of claim 6, wherein:
   the signal transfer element is configured to transfer to the data processing system a synchronous signal; and
   the data processing system is configured to begin measuring, processing, and digitizing upon receiving the synchronous signal.

10. The skin potential measuring sensor of claim 6, wherein the measuring electrode is a single use electrode.

11. A distributed architecture system for measuring skin potential, comprising at least two skin potential measuring sensors and a main processor, wherein each of the skin potential measuring sensors comprises:
    a measuring electrode configured to be placed on the skin at a measurement point to provide an analog signal;
    a data processing system placed on and continuously connected directly to the measuring electrode at the measurement point, wherein the data processing system is configured to measure, process, and digitize the analog signal provided by the measuring electrode to provide a measured digital signal; and
    a signal transfer element connected to the data processing system and configured to transfer the measured digital signal, wherein:
      the main processor is configured to simultaneously sample, collect and/or analyze the measured digital signal from each of the at least two skin potential measuring sensors.

12. The system for measuring skin potential of claim 11, further comprising a data transfer network, wherein the signal transfer element of each of the at least two skin potential measuring sensors is configured to interface with the data transfer network to transfer the measured digital signal in a digital form to the data transfer network to the main processor.

13. The system for measuring skin potential of claim 12, wherein:
    the data transfer network is configured to transfer to the signal transfer element of each of the at least two skin potential measuring sensors a synchronous signal from the main processor; and the data processing system of each of the at least two skin potential measuring sensors is configured to begin measuring, processing, and digitizing upon receiving the synchronous signal from the main processor.

14. The system for measuring skin potential of claim 11, wherein:

the signal transfer element of each of the at least two skin potential measuring sensors is configured to transfer to the data processing system of each of the at least two skin potential measuring sensors a synchronous signal from the main processor; and the data processing system of each of the at least two skin potential measuring sensors is configured to begin measuring, processing, and digitizing upon receiving the synchronous signal from the main processor.

15. The system for measuring skin potential of claim 11, wherein the main processor simultaneously samples, collects and/or analyzes the measured digital signal from each of the at least two skin potential measuring sensors synchronously and independently to allow numeric calculation and/or formation of new signals through calculation without additional electronics.

* * * * *